(12) United States Patent
Maniere

(10) Patent No.: US 8,979,945 B2
(45) Date of Patent: Mar. 17, 2015

(54) IMPLANTABLE END PAD

(76) Inventor: Gordon Maniere, St. Clair Shores, MI (US)

( * ) Notice: Subject to any disclaimer, the term of this patent is extended or adjusted under 35 U.S.C. 154(b) by 0 days.

(21) Appl. No.: 13/527,675

(22) Filed: Jun. 20, 2012

(65) Prior Publication Data

US 2012/0323340 A1 Dec. 20, 2012

Related U.S. Application Data

(60) Provisional application No. 61/498,670, filed on Jun. 20, 2011.

(51) Int. Cl.
- *A61F 2/78* (2006.01)
- *A61F 2/28* (2006.01)
- *A61F 2/80* (2006.01)

(52) U.S. Cl.
CPC ............... *A61F 2/78* (2013.01); *A61F 2/2814* (2013.01); *A61F 2002/7806* (2013.01); *A61F 2/80* (2013.01); *A61F 2210/0071* (2013.01); *A61F 2230/0071* (2013.01); *A61F 2002/7887* (2013.01)
USPC .............................. 623/32; 632/16.11; 632/33

(58) Field of Classification Search
CPC .. A61F 2/2814; A61F 2002/7887; A61F 2/78
USPC .............. 623/16.11, 18.11, 27, 32, 33, 38, 57
See application file for complete search history.

(56) References Cited

U.S. PATENT DOCUMENTS

| | | | | |
|---|---|---|---|---|
| 4,007,494 A | * | 2/1977 | Sauer | 623/23.12 |
| 4,778,470 A | * | 10/1988 | Antebi | 623/27 |
| 4,781,720 A | * | 11/1988 | Sherva-Parker | 623/27 |
| 5,024,670 A | * | 6/1991 | Smith et al. | 128/898 |
| 6,709,466 B1 | * | 3/2004 | Grundei | 623/32 |
| 7,150,761 B2 | * | 12/2006 | Justin et al. | 623/20.14 |
| 2006/0173547 A1 | * | 8/2006 | Ensign | 623/20.15 |
| 2007/0162150 A1 | * | 7/2007 | Fago et al. | 623/23.42 |

FOREIGN PATENT DOCUMENTS

| | | | | |
|---|---|---|---|---|
| DE | 3125268 | * | 1/1983 | |
| EP | 1508317 | * | 5/2004 | |

* cited by examiner

*Primary Examiner* — Marcia Watkins
(74) *Attorney, Agent, or Firm* — Carlson, Gaskey & Olds P.C.

(57) ABSTRACT

Disclosed is an implantable end pad. The end pad includes a bone attachment portion having a recess configured to receive an amputated bone of a residual limb. The end pad further includes an end portion having a contour corresponding to at least a portion of a socket of an artificial limb such that the end pad can be at least partially received in the socket of the residual limb. Further disclosed is a method wherein the end pad is implanted into a residual limb by way of a surgical procedure.

19 Claims, 7 Drawing Sheets

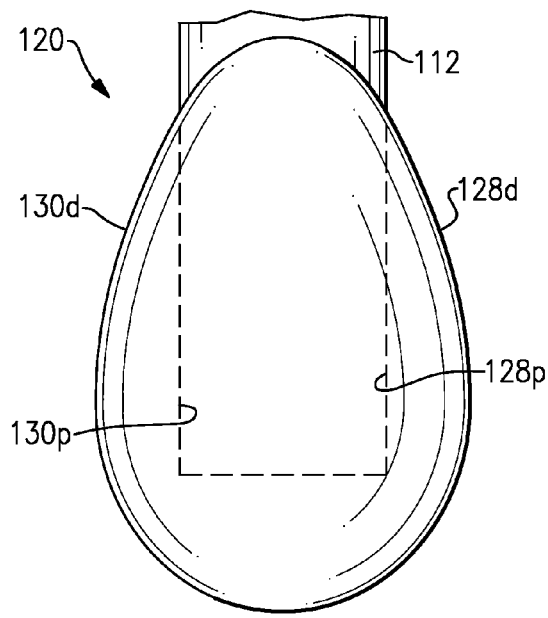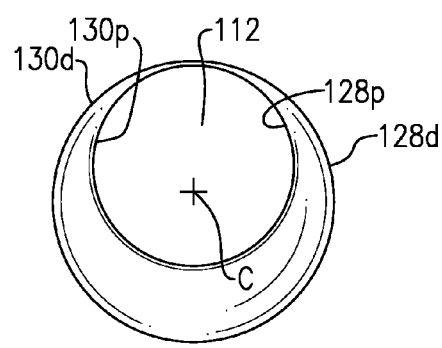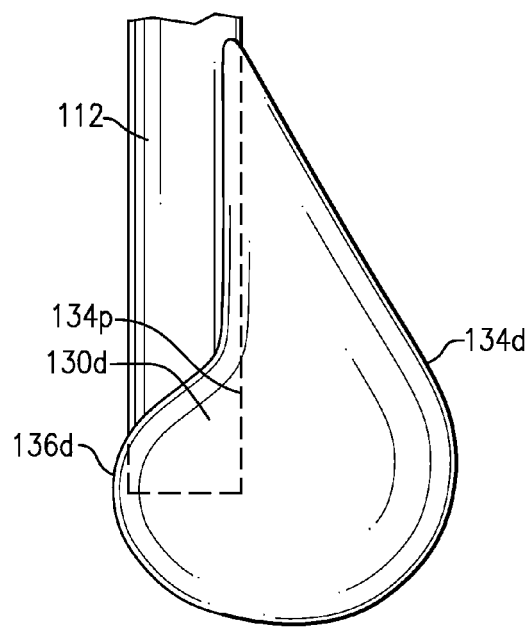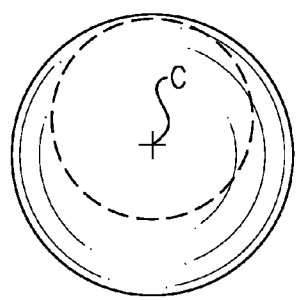
FIG.4A
FIG.4B
FIG.4C
FIG.4D

IMPLANTABLE END PAD

RELATED APPLICATIONS

This application claims the benefit of U.S. Provisional Application No. 61/498,670, filed 20 Jun. 2011, the entirety of which is herein incorporated by reference.

BACKGROUND

This disclosure relates to an implantable end pad that helps secure an artificial limb to a residual limb of an amputee.

Artificial, or prosthetic, limbs are typically used to replace parts lost by injury. Artificial limbs are known to include sockets sized to receive an amputee's residual limb.

FIG. 1 is representative of a typical residual limb 1, including an amputated bone 2 and various soft tissue 4. In the prior art, an artificial limb 6 may be custom fit for the residual limb 1, such that the socket 8 is sized to receive the residual limb 1. The residual limb 1 may be a leg amputated below or above the knee, or an arm amputated below or above the elbow, as examples. The artificial limb 6 is selected to correspond to the particular residual limb 1 and to provide a desired level of performance. The residual limb 1 may be fit with a liner or other interface to provide padding between the residual limb 1 and the socket 8. The liner may be positioned within the socket 8 between the soft tissue 4 and the artificial limb 6.

SUMMARY

Disclosed is an implantable end pad. The end pad includes a bone attachment portion having a recess configured to receive an amputated bone of a residual limb. The end pad further includes an end portion having a contour corresponding to at least a portion of a socket of an artificial limb such that the end pad can be at least partially received in the socket of the residual limb. Further disclosed is a method wherein the end pad is implanted at least partially into a residual limb by way of a surgical procedure.

BRIEF DESCRIPTION OF THE DRAWINGS

The drawings that accompany the following detailed description can be briefly described as follows:

FIG. 4A is an anterior view of another example end pad that may be used with transtibial amputees;

FIG. 4B is a superior view of the end pad of FIG. 4A;

FIG. 4C is a lateral view of the end pad of FIG. 4A;

FIG. 4D is an inferior view of the end pad of FIG. 4A;

DETAILED DESCRIPTION

Figures 1, 2:
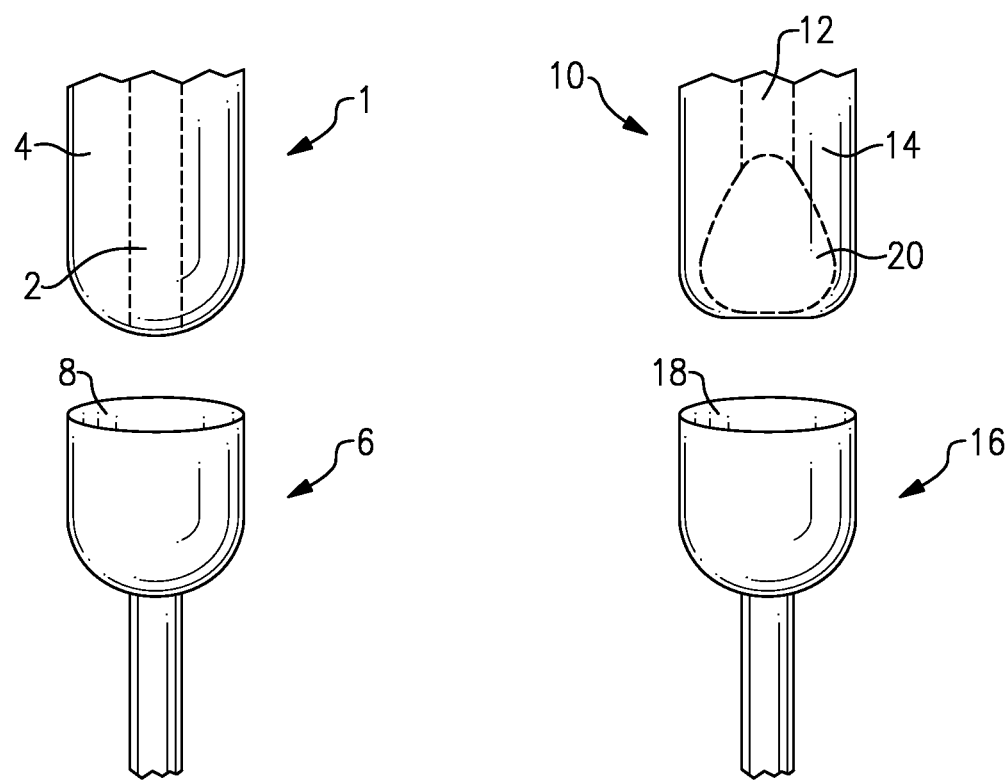
FIG. 1 illustrates a prior art artificial limb receiving a residual limb.
FIG. 2 illustrates an artificial limb receiving a residual limb having an example end pad.

FIG. 2 is representative of a residual limb 10, including an amputated bone 12 and various soft tissue 14. In most examples, an artificial limb 16 is custom-fit for the particular residual limb 10, such that the socket 18 is sized to receive the residual limb 10.

In the example shown, an end pad 20 is received over an end of the amputated bone 12. The perimeter of the end pad 20 is generally shaped to correspond to the socket 18. As will be appreciated from the below, the term "correspond" as used herein means that at least a portion of the contour of the end pad 20 is shaped in a manner that mimics at least a portion of the curvature of an expected socket 18, such that the end pad 20 provides a desired fit with the socket 18.

In one example, the end pad 20 is implanted within the soft tissue 14 directly adjacent to the amputated bone 12. When the artificial limb 16 is attached to the residual limb 10, the socket 18 receives at least some of the end pad 20. As shown, the example end pad 20 is encapsulated within the soft tissue 14. In another example, a portion of the end pad 20 is exposed. Still, in further examples, the end pad 20 may be exposed such that the end pad 20 can directly engage the socket 18. Attachment features could be provided between the end pad 20 and the socket 18 in this case, to provide a desired fit between the end pad 20 and the socket 18. Such attachment features include placing padding (such as a sleeve) between the end pad 20 and the socket 18, or placing some type of fastener between the end pad 20 and the socket 18.

Figure 3A:
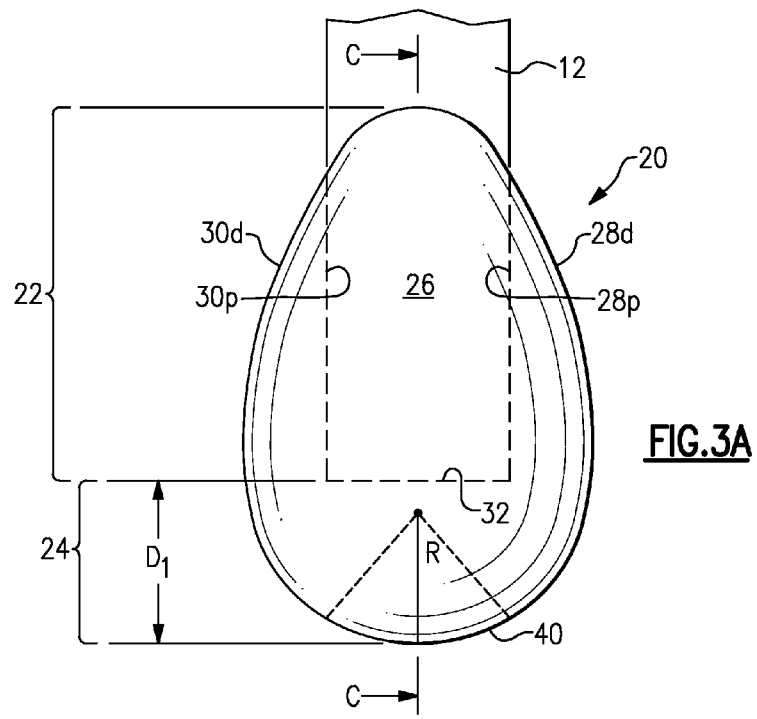
FIG. 3A is an anterior view of the FIG. 2 end pad.
Figure 3B:
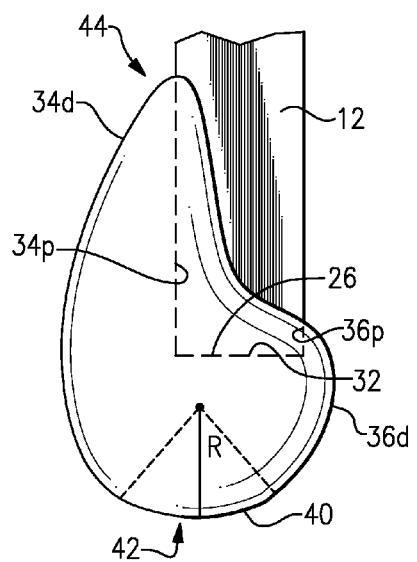
FIG. 3B is representative of either a lateral or medial view of the FIG. 3A end pad.

FIGS. 3A-3B show the end pad 20 in further detail. For example, the end pad 20 generally includes a bone attachment portion 22 and an end portion 24 opposite the bone attachment portion 22. The bone attachment portion 22 has a recess 26 for receiving the amputated bone 12. The recess 26 may be defined between proximal (or inner, relative to the center C of the end pad 20) medial and lateral surfaces 28p, 30p as well as a base surface 32, and the proximal anterior and posterior surfaces 34p, 36p.

The lower end portion 24 may extend a distance D1, which can be as much as 25 mm (approximately 0.98 in) or 50 mm (approximately 1.97 in), below the bone attachment portion 22 (or, as shown, below the base surface 32), and is semi-spherical having an convex outer contour 40 generally defined by a radius R at an inferior surface 42 thereof. The radius R is selected to correspond to the concavity of the socket 18 and to encapsulate the end of the amputated bone 12. While the lower end portion 24 is shown as being semi-spherical, the shape of the lower end portion 24 can be varied to correspond to different sockets 18.

In the example shown, the distal (or outer) surface of the end pad 20 smoothly and continuously extends from its inferior surface 42 to its superior surface 44. The exterior of the end pad 20 is further defined by distal (or outer, relative to the center C of the end pad 20) medial, lateral, anterior and posterior surfaces 28d, 30d, 34d, 36d, respectively.

The end pad 20 may be implanted surgically by way of a surgeon attaching the end pad 20 to the amputated bone 12 immediately following amputation. This may be desirable, as the end pad 20 can be attached without requiring a patient to undergo multiple surgeries. However, the end pad 20 can be implanted post-amputation with a separate surgery.

Figure 3C:
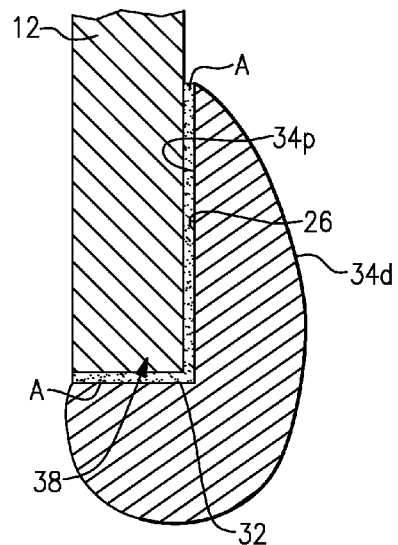
FIG. 3C is a representative cross sectional view at line C-C showing an example of how an amputated bone attaches to the disclosed end pad.
Figure 5A:
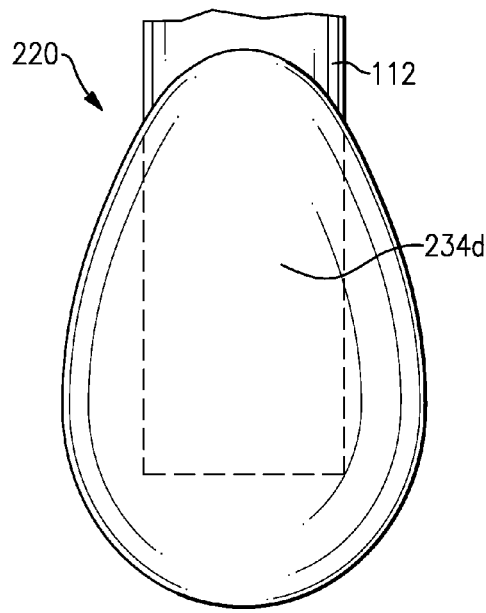
FIG. 5A is an anterior view of yet another example end pad that may be used with transfemoral amputees.
Figure 5B:
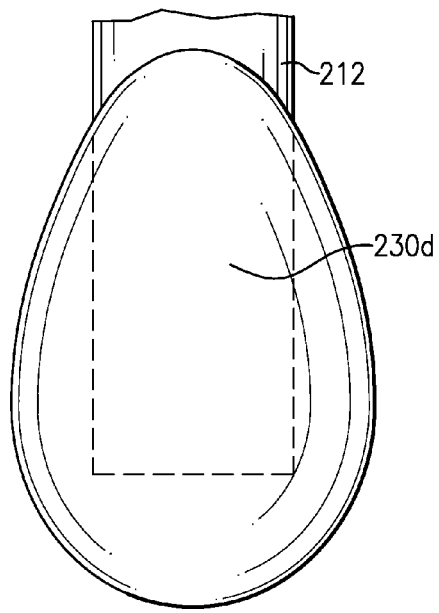
FIG. 5B is a lateral view of the end pad of FIG. 5A.
Figure 5C:
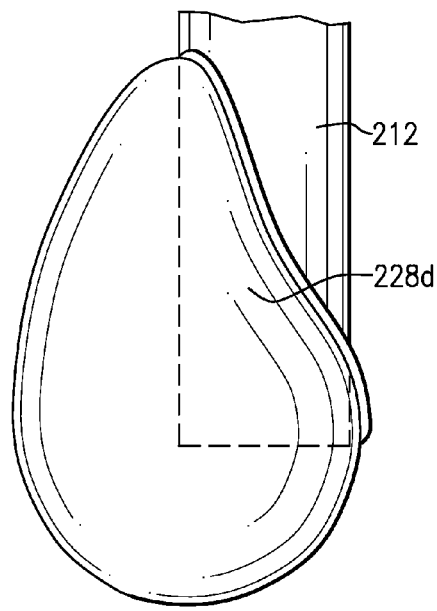
FIG. 5C is a medial view of the end pad of FIG. 5A.
Figure 5D:
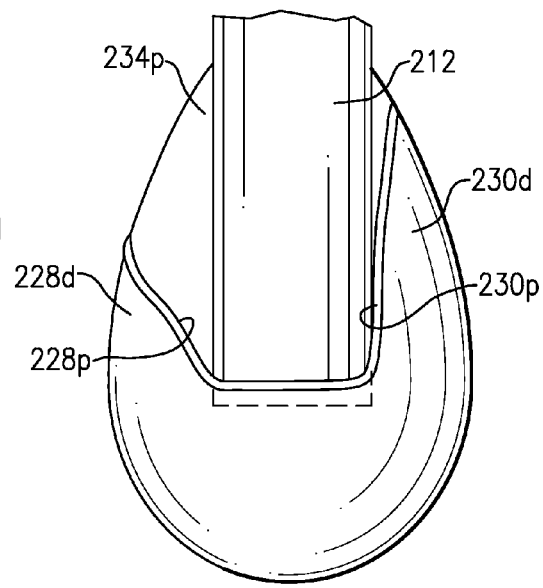
FIG. 5D is a posterior view of the end pad of FIG. 5A.
Figure 7:
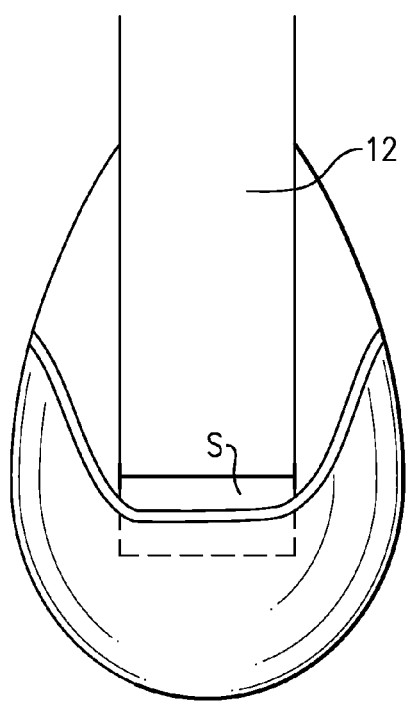
FIG. 7 is representative of another example end pad having a spacer intermediate the end pad and an amputated bone.
Figure 8:
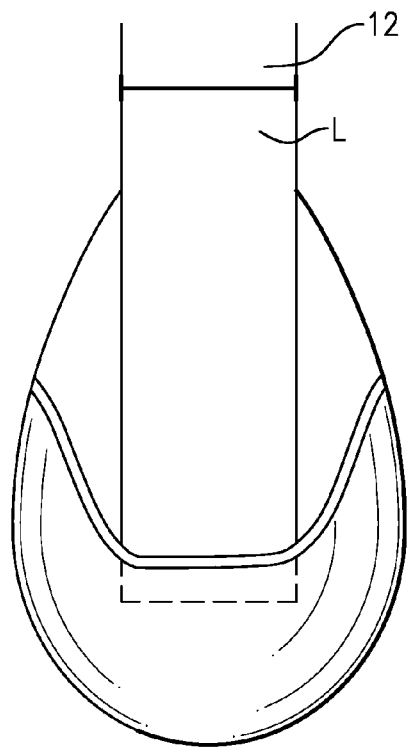
FIG. 8 is representative of yet another example end pad having a liner intermediate the end pad and an amputated bone.

In either case, an example surgical procedure would involve a surgeon displacing the soft tissue 14 to sufficiently expose the bone 12. The surgeon may essentially "trim" the distal end 38 of the amputated bone 12 so that it continuously engages the base surface 32. The recess 26 of the end pad 20 receives the end of the amputated bone 12. A surgical adhesive A is then used to bond the amputated bone 12 to the end pad 20, as shown in FIG. 3C. The surgical adhesive A may be MediSil, for example, or another known surgical adhesive or gel. While the example end pad 20 is attached directly adjacent the amputated bone 12 via the surgical adhesive A, the end pad 20 could be indirectly attached to the amputated bone 12, by way of an intermediate spacer S or liner L, as examples (represented in FIGS. 7-8). In yet another example, the end pad 20 could be held exclusively with soft tissue 14 completely independent from the amputated bone 12 or any bone.

It is further contemplated, within the scope of this disclosure, that an implanted end pad 20 could be removed and replaced with another end pad of another size. For example, in the case where atrophy of the soft tissue 14 causes an undesirable fit between the end pad 20 and the socket 18 of the artificial limb 16, the end pad 20 can be replaced with an end pad larger in size. The end pad 20 could also, in another example, be resizable by way of the injection or removal of medical grade fluid (such as silicone).

FIGS. 4A-4D, 5A-5D and 6A-6C show three embodiments of the end pad 20, as generally explained below. Numerals in these three embodiments generally relate to those from FIGS. 3A-3B, above, however they include a preappended "1," "2," or "3."

With reference to FIGS. 4A-4D, the end pad 120 in this example is for use with transtibial, or below the knee, amputees. Due to the nature of a below the knee amputation, the distal and proximal medial and lateral surfaces 128d, 128p, 130d, 130p are generally mirror images of one another about the center C of the end pad 120 (e.g., the medial and lateral surfaces are substantially the same size and shape).

FIGS. 5A-5D show an end pad 220 adapted for use with transfemoral, or above the knee, amputees. Notably, in this example, the distal and proximal lateral surfaces 230d, 230p are more pronounced than the distal and proximal medial surface 228d, 228p. Whereas in the FIGS. 4A-4D example an even distribution of surgical adhesive A may be preferred, in this example, due to the inherent stresses and forces on a transfemoral amputee, the majority of the surgical adhesive A is desired between the amputated bone 212, and the proximal lateral and proximal anterior surfaces 230p, 234p.

Figure 6A:
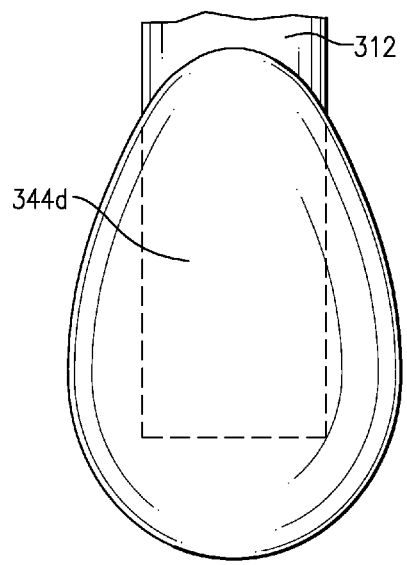
FIG. 6A is a superior view of yet another example end pad that may be used with transradial or transhumeral amputees.
Figure 6B:
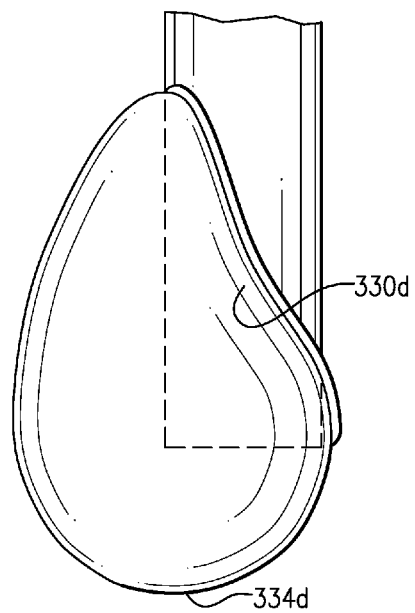
FIG. 6B is a lateral view of the end pad of FIG. 6A.
Figure 6C:
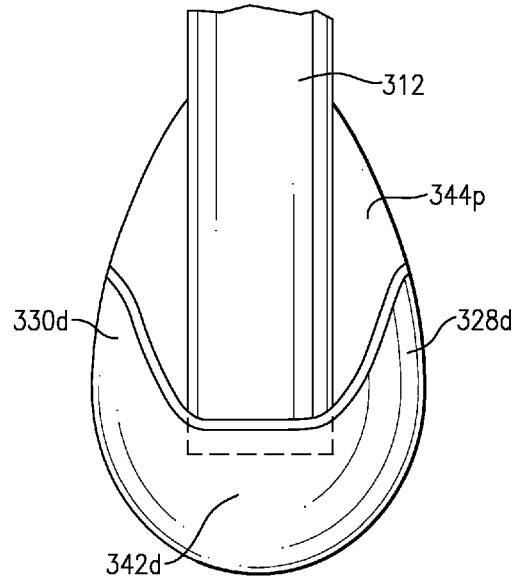
FIG. 6C is an inferior view of the end pad of FIG. 6A.

FIGS. 6A-6C are representative of an end pad 320 for transradial (below the elbow) or transhumeral (above the elbow) amputees. In this instance, it is desired to apply the majority of the surgical adhesive A between the amputated bone 312 and proximal superior surface 344p so that the most padding is provided at the distal superior surface 344d. As in the example of FIGS. 4A-4D, the medial and lateral surfaces 328, 330 are generally mirror images of one another. Notably, in this example, the socket 18 of an artificial limb 10 (in this case an arm), would attach to the distal posterior surface 334d, unlike in the prior two examples where it would attach to the inferior surface 42.

Figure 9A:
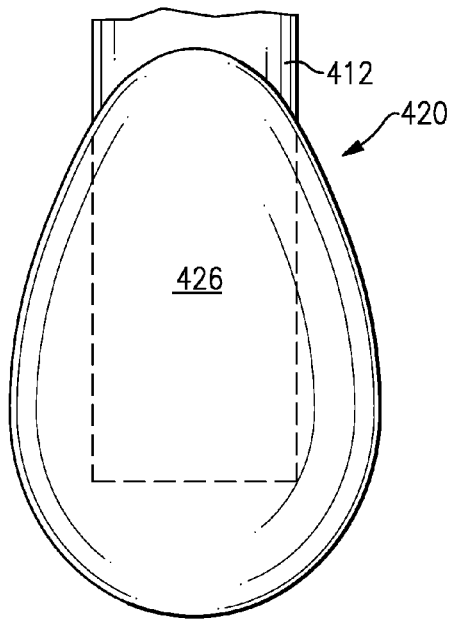
FIG. 9A is a front view of another example end pad.
Figure 9B:
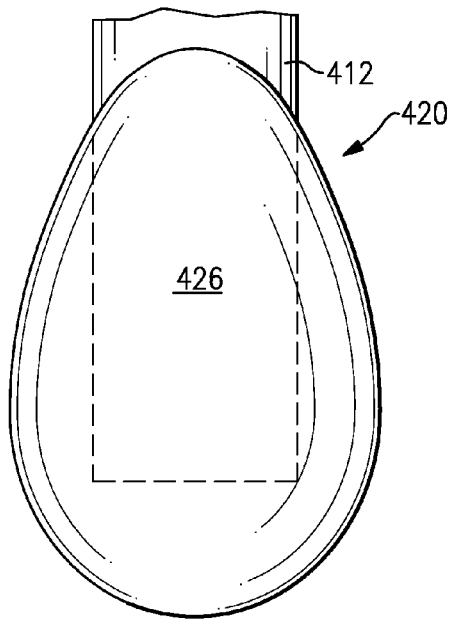
FIG. 9B is a rear view of the FIG. 9A end pad.
Figure 9C:
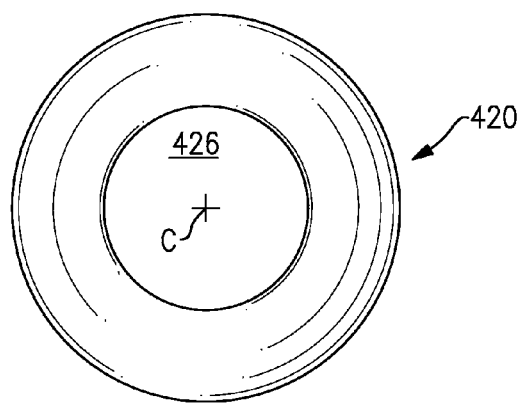
FIG. 9C is a top view of the FIG. 9A end pad.

FIGS. 9A-C show another example end pad 420. The numerals in FIGS. 9A-9C correspond to those in FIGS. 3A-3C, above, with a preappended "4." While the end pads 120, 220, and 320 are each shaped to correspond to a particular residual limb 112, 212, 312, the end pad 420 may be "universal," in that it can be used with any residual limb 412. As shown, the end pad 420 is generally symmetrical about its center C, and thus its front and rear views are substantially the same (e.g., FIGS. 9A and 9B). The distal surfaces of the end pad 420 generally provide the end pad 420 with a "teardrop" shape. Similar to the above embodiments, the residual limb 412 can be received within the recess 426 (e.g., using adhesive A, as noted above). Accordingly, the disclosed end pad 20 can have a variety of shapes, including, but not limited to, those shown in the FIGS. 3A-9C.

Use of the disclosed end pad substantially absorbs shock and force on the amputee's residual limb, thereby increasing quality of life and allowing the amputee to walk and run longer with little to no pain. The end pad further reduces bone spurs in the amputated bone, and may restore bone canal pressure inside the amputated bone.

The disclosed end pad may be made of one or more appropriate materials including any number of medical grade silicones, polyurethanes, thermoplastic elastomers (TPEs), ultra high molecular weight polyethylenes (UHMWPEs), or polyetheretherketones (PEEKs) to name a few. The end pad could be formed of an appropriate hybrid biomaterial combination. At any rate, the selected material provides the amputee with adequate shock and force absorption, as noted above.

Terms such as "distal," "proximal," "anterior," "posterior," "superior," "inferior," "lateral," and "medial" are to be construed as they would by one of ordinary skill in this art to the extent they are not otherwise defined herein. Often, in the medical field, these terms are used relative to the center of the human body. However, at certain points in this disclosure, these terms are used with reference to the center of the end pad itself, because the end pad can be used on various limbs on either side of the body. These terms are not limiting, however, and are merely used to aid in describing the structure of the various example end pads disclosed. For example, the terms "lateral" and "medial" are used to distinguish the different sides of the end pad, and are not meant to imply any specific orientation of the end pad relative to the human body.

Although the different examples have the specific components shown in the illustrations, embodiments of this invention are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. An artificial limb assembly, comprising:
   an end pad adapted to be implanted beneath soft tissue such that the end pad is completely encapsulated by the soft tissue, the end pad further being adapted to be attached to an end of an amputated bone, wherein the end pad is asymmetrical about a central axis thereof, the end pad including a recess adapted to receive the end of the amputated bone, wherein the end pad including the recess is provided by a single, continuous piece of polymer material, and wherein an inferior most surface of the end pad has a convex outer contour providing a semi-spherical shape, the outer contour of the inferior most surface corresponding to a contour of the socket; and
   an artificial limb including a socket, the socket adapted to receive the end pad such that the soft tissue is provided between the end pad and the socket, and wherein the outer contour of the inferior most surface is defined by a constant radius, the radius having an origin along a center line of the end pad.

2. The artificial limb assembly as recited in claim 1, wherein a spacer is provided between the amputated bone and the end pad.

3. The artificial limb assembly as recited in claim 1, wherein a liner is provided between the amputated bone and the end pad.

4. The artificial limb assembly as recited in claim 1, wherein the end pad is adapted to be attached to the amputated bone by way of a surgical adhesive.

5. The artificial limb assembly as recited in claim 1, wherein the contour provides a superior surface and the contour smoothly extends from the inferior most surface to the superior surface of the end pad.

6. The artificial limb assembly as recited in claim 1, wherein the end pad is asymmetrical when the residual limb is provided by one of an above the knee, below the elbow, and an above the elbow amputation.

7. The artificial limb assembly as recited in claim 1, wherein medial and lateral surfaces of the end pad are the same size and shape.

8. The artificial limb assembly as recited in claim 1, wherein the end portion extends below the bone attachment portion by a distance within a range of 25 mm and 50 mm.

9. The artificial limb assembly as recited in claim 1, wherein the end pad is configured to support soft tissue of the residual limb.

10. The artificial limb assembly as recited in claim 1, wherein the end pad is entirely made of a medical grade silicone.

11. The artificial limb assembly as recited in claim 1, wherein the end pad is entirely made of a material selected from one of polyurethanes, thermoplastic elastomers (TPEs), ultra high molecular weight polyethylenes (UHMWPEs), and polyetheretherketones (PEEKs).

12. The artificial limb assembly as recited in claim 1, wherein the entirety of the end pad is adapted to be spaced-apart from the socket by the soft tissue.

13. The artificial limb assembly as recited in claim 12, wherein an outer surface of the end pad is adapted to directly contact the soft tissue.

14. The artificial limb assembly as recited in claim 1, wherein the socket includes a concave inner surface.

15. The artificial limb assembly as recited in claim 4, wherein an outer surface of the amputated bone is adapted to be directly attached to the end pad by way of the adhesive, such that the adhesive directly contacts the amputated bone and the end pad.

16. An artificial limb assembly, comprising:
an end pad adapted to be implanted beneath soft tissue and attached to an end of an amputated bone, the end pad including a recess adapted to receive the end of the amputated bone, wherein the end pad is asymmetrical about a central axis thereof, wherein the end pad including the recess is provided by a single, continuous piece of polymer material, and wherein an inferior most surface of the end pad has a convex outer contour providing a semi-spherical shape defined by a constant radius, the radius having an origin along a centerline of the end pad, the outer contour of the inferior surface corresponding to a contour of a socket; and
an artificial limb including the socket adapted to receive the end pad such that the soft tissue is provided between the end pad and the socket.

17. The artificial limb assembly as recited in claim 16, wherein the end pad is adapted to be attached to the amputated bone by way of a surgical adhesive.

18. The artificial limb assembly as recited in claim 16, wherein an exterior surface of the end pad is defined, relative to a center of the end pad, by distal medial, distal lateral, distal anterior and distal posterior surfaces, and wherein the distal anterior surface is more pronounced than the distal posterior surface.

19. The artificial limb assembly as recited in claim 16, wherein the end pad is adapted to be implanted beneath soft tissue such that the end pad is completely encapsulated by the soft tissue.

* * * * *